US006978724B2

(12) United States Patent
Anderson et al.

(10) Patent No.: US 6,978,724 B2
(45) Date of Patent: Dec. 27, 2005

(54) COPPER COMPLEXES AND THEIR USE AS WOOD PRESERVATIVES

(75) Inventors: Albert Gordon Anderson, Wilmington, DE (US); Mark A. Scialdone, Oxford, PA (US)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/699,329

(22) Filed: Oct. 31, 2003

(65) Prior Publication Data

US 2004/0089196 A1 May 13, 2004

Related U.S. Application Data

(60) Provisional application No. 60/423,255, filed on Nov. 1, 2002.

(51) Int. Cl.[7] ........................ A01N 55/02; A01N 33/00; A01N 57/00; B27K 3/22; B27K 5/20
(52) U.S. Cl. ..................... 109/18.32; 162/160; 162/161; 424/632; 424/634; 424/637; 424/638; 427/297; 427/421.1; 427/428.1; 427/429; 427/439; 427/440; 428/35.6; 428/292.4; 428/532; 428/537.1; 428/537.5
(58) Field of Search ....................... 106/18.32; 162/160, 162/161; 424/632, 634, 637, 638, 297, 421, 429, 439; 427/297, 421.1, 428.1, 429, 439, 440; 428/35.6, 292.4, 532, 537.1, 537.5

(56) References Cited

U.S. PATENT DOCUMENTS

| | | | | |
|---|---|---|---|---|
| 4,420,542 A | * | 12/1983 | Sowers | 428/541 |
| 4,759,872 A | * | 7/1988 | Marx et al. | 252/400.53 |
| 5,342,438 A | * | 8/1994 | West | 106/18.3 |
| 5,426,121 A | * | 6/1995 | Bell | 514/500 |
| 6,306,202 B1 | * | 10/2001 | West | 106/18.3 |
| 6,340,384 B1 | * | 1/2002 | Walker | 106/18.32 |
| 6,352,583 B1 | * | 3/2002 | Goettsche et al. | 106/18.32 |
| 6,686,056 B2 | * | 2/2004 | Roos et al. | 428/535 |

FOREIGN PATENT DOCUMENTS

EP 000864406 A2 * 9/1998
EP 000789511 B1 * 3/2000

* cited by examiner

Primary Examiner—Anthony J. Green

(57) ABSTRACT

This invention relates to copper complexes that significantly reduce the decay of wood, cellulose, hemicellulose, and lignin caused by fungi. A process for treating such materials with these copper-containing anti-fungal agents is also disclosed.

27 Claims, 2 Drawing Sheets

COPPER COMPLEXES AND THEIR USE AS WOOD PRESERVATIVES

CROSS REFERENCE TO RELATED APPLICATIONS

This application claims the benefit of U.S. Provisional Application No. 60/423,255, filed Nov. 1, 2002, the disclosure of which is incorporated herein, in its entirety, by reference.

FIELD OF THE INVENTION

This invention relates to copper complexes that significantly reduce the decay of wood, cellulose, hemicellulose and lignin caused by fungi.

BACKGROUND OF THE INVENTION

The decay of wood and cellulose by fungi causes significant economic loss. Until recently, the most widely used wood preservative has been chromated copper arsenate (CCA). However, issues have been raised concerning the environmental impact of arsenic and chromium used in CCA-treated lumber. To address these issues, arsenic- and chromium-free wood preservatives are sought.

Wood preservation formulations containing copper-chelating molecules are known in the art. One such preservative system is based on a copper complex, Cu-HDO, which contains a bidentate ligand, N-nitrosylated cyclohexyl-hydroxylamine (DE 3,835,370). Another alternative wood preservative is ACQ, an Ammoniacal Copper Quaternary compound (U.S. Pat. No. 4,929,454).

Many metal-chelating functionalities are known, causing a central metal ion to be attached by coordination links to two or more nonmetal atoms (ligands) in the same molecule. Heterocyclic rings are formed with the central (metal) atom as part of each ring. Polyhydroxamic acids are known and have been shown to complex with copper. Amidoxime or hydroxamic acids of cyanoethylated cellulose are known as complexation agents for metal ions, including copper (Altas H. Basta, *International Journal of Polymeric Materials*, 42, 1–26 (1998)).

In spite of these and other attempts to develop CCA alternatives, there remains a need for improved wood preservatives.

SUMMARY OF THE INVENTION

This invention relates to a wood preservative composition comprising an aqueous solution of:

a. a copper complex comprising copper and a chelating compound comprising at least two functional groups selected from the group of amidoxime, hydroxamic acid, thiohydroxamic acid, N-hydroxyurea, N-hydroxycarbamate, and N-nitroso-alkyl-hydroxylamine; and b. ammonia, ethanolamine, or pyridine in an amount sufficient to solubilize the copper complex of (a).

This invention also relates to a process for preparing a wood preservative copper complex, comprising:

a. forming an aqueous mixture of a cyanoethylation catalyst and an alcohol or amine;

b. adding an unsaturated nitrile to the aqueous mixture of (a);

c. adding a source of hydroxylamine, together with ammonium hydroxide, ethanolamine, or pyridine, to the aqueous mixture of (b) to form an aqueous solution of a cyanoethylated derivative of the alcohol or amine; and d. adding a source of Cu(II) to the aqueous solution of (c) to form a wood preservative copper complex.

This invention also relates to a process for preserving wood, lumber, plywood, oriented strandboard, cellulose, hemicellulose, lignin, cotton, or paper by contacting such materials with the wood preservative composition of this invention.

This invention also relates to articles treated by the preservation process of this invention.

This invention also relates to articles of wood, lumber, plywood, oriented strandboard, paper, cellulose, cotton, lignin or hemicellulose which further comprise copper and a chelating compound comprising at least two functional groups selected from the group of amidoxime, hydroxamic acid, thiohydroxamic acid, N-hydroxyurea, N-hydroxycarbamate, and N-nitroso-alkyl-hydroxylamine.

DETAILED DESCRIPTION OF THE INVENTION

Figure 1A:
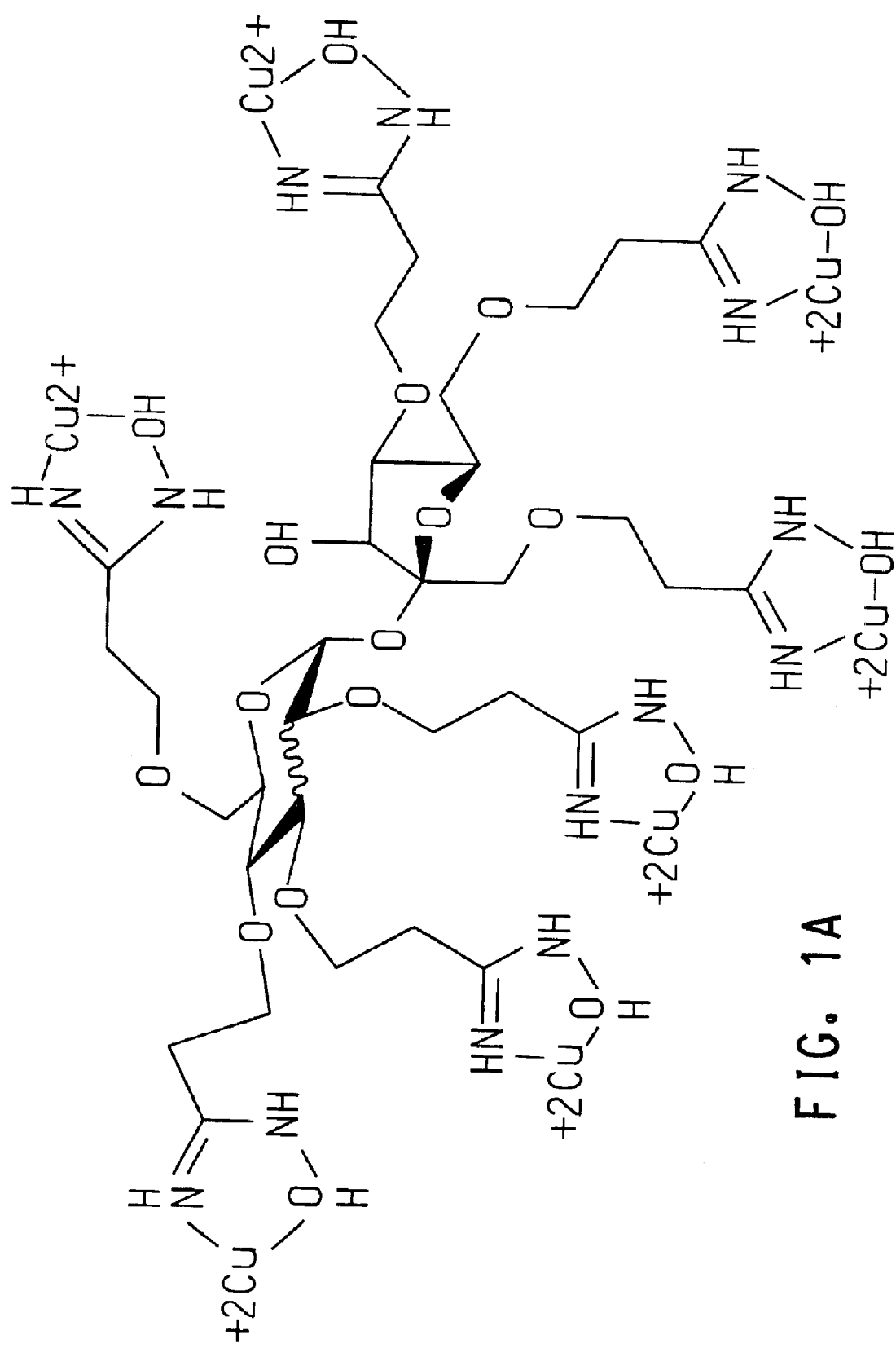
FIG. 1a shows the chemical structure of the copper complex of amidoximes of sucrose (Cu—Am-Suc7).

Applicants have discovered that copper complexes of chelating compounds with two or more appropriate functional groups can be prepared and rendered soluble in aqueous solution by the addition of ammonia, ethanolamine, or pyridine. These solubilized copper complexes can subsequently be imbibed into wood. Upon loss or evaporation of ammonia, ethanolamine, or pyridine, these copper complexes become insoluble, thereby fixing the copper ions within the wood. Upon evaporation of the ammonia, ethanolamine, or pyridine, the copper complexes of this invention bind tenaciously to cellulose. Wood products such as lumber, plywood, oriented strandboard, cellulose, hemicellulose, lignin, cotton, and paper can also be treated with the wood preservative compositions of this invention. The treated materials (including wood, paper, cellulose, cotton, lignin and hemicellulose) are resistant to fungal attack and are thus preserved.

Suitable chelating compounds for use in this invention have two or more multidentate chelating groups such as amidoxime, hydroxamic acid, thiohydroxamic acid, N-hydroxyurea, N-hydroxycarbamate and N-nitroso-alkyl-hydroxylamine groups. These functional groups can be introduced by the methods described herein or by methods known in the art.

For example, amidoximes can be prepared by the reaction of nitrile-containing compounds with hydroxylamine. (Eqn. 1)

Eqn. 1

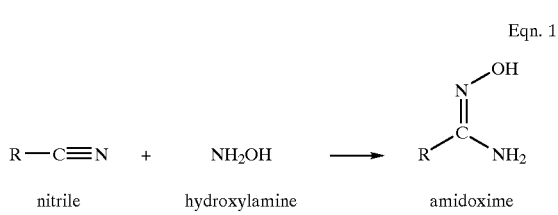

nitrile + hydroxylamine → amidoxime

Hydroxamic acids are also well known (H. L. Yale, "The Hydroxamic Acids", *Chem. Rev.*, 209–256 (1943)). Polymers containing hydroxamic acid groups are known and can be prepared by addition of hydroxylamine to anhydride groups of anhydride-containing copolymers, such as styrene-maleic anhydride copolymer or poly(vinylmethylether/maleic anhydride) copolymers, or by reaction of hydroxylamine with ester groups. Hydroxamic acid-containing polymers can also be prepared by acid-catalyzed hydrolysis of polymers that contain amidoxime groups (U.S. Pat.No. 3,345,344).

Thiohydroxamic acids can be prepared by addition of hydroxylamine to dithiocarboxylic acids (H. L. Yale, *Chem. Rev.*, 33, 209–256 (1943)).

N-hydroxyureas can be prepared by reaction of hydroxylamine with an isocyanate (A. O. Ilvespaa et al., *Chime (Switz.)* 18, 1–16 (1964)).

N-Hydroxycarbamates can be prepared by reaction of hydroxylamine with either a linear or cyclic carbonate (A. O. Ilvespaa et al., *Chimia (Switz.)* 18, 1–16 (1964)).

N-Nitroso-alkyl-hydroxylamines can be prepared by nitrosation of alkyl hydroxylamines (M. Shiino et al., *Bioorganic and Medicinal Chemistry* 95, 1233–1240 (2001)).

Preferred chelating compounds are those which contain two or more amidoxime and/or hydroxamic acid groups. The amidoxime functionality can be readily converted to the corresponding hydroxamic acid functionality in aqueous solution, a reaction that is catalyzed by acid.

A convenient route to this preferred class of chelating compounds (i.e., amidoximes and hydroxamic acids) is by adding hydroxylamine to the corresponding nitrile compound. There are several methods known for preparing nitrile-containing compounds, including cyanide addition reactions such as hydrocyanation, polymerization of nitrile-containing monomers to form polyacrylonitrile or copolymers of acrylonitrile with vinyl monomers, and dehydration of amides. Typical procedures for the syntheses of nitriles may be found in J. March, Advanced Organic Chemistry, 4$^{th}$ ed., John Wiley and Sons, NY, (1992).

A particularly useful route to nitrites is termed "cyanoethylation", in which acrylonitrile undergoes a conjugate addition reaction with protic nucleophiles such as alcohols and amines (Eqn. 2). Other unsaturated nitrites can also be used in place of acrylonitrile.

Eqn. 2

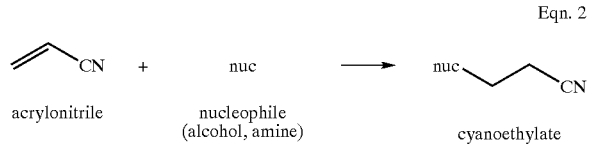

acrylonitrile     nucleophile (alcohol, amine)     cyanoethylate

Preferred amines for the cyanoethylation reaction are primary amines and secondary amines having 1 to 30 carbon atoms, and polyethylene amine. Alcohols can be primary, secondary, or tertiary. The cyanoethylation reaction (or "cyanoalkylation" using an unsaturated nitrile other than acrylonitrile) is preferably carried out in the presence of a cyanoethylation catalyst. Preferred cyanoethylation catalysts include lithium hydroxide, sodium hydroxide, and potassium hydroxide. The amount of catalyst used is typically between 0.05 mol % and 15 mol %, based on unsaturated nitrile.

A wide variety of materials can be cyanoethylated. The cyanoethylates can be derived from the reaction of acrylonitrile with carbohydrates such as regenerated cellulose, dextran, dextrin, gums (guar, locust bean, honey locust, flame tree, tara, arabic, tragacanth, and karaya); starches (corn, potato, tapioca and wheat); or modified natural polymers such as cellulose xanthate, dimethylthiourethane of cellulose, ethyl cellulose, ethylthiourethane of cellulose, hydroxyethylcellulose, methylcellulose, and phenylthiourethane of cellulose. Other natural polymers that have been cyanoethylated include flax, jute, manila, sisal, and proteins such as blood albumin, casein, gelatin, gluten, soybean protein, wool, and corn zein, or materials derived from such natural polymers. Pre-treatment of high molecular weight or water-insoluble carbohydrates and starches with enzymes may be used if necessary to increase the solubility of the amidoxime or hydroxamic acid copper complex in an aqueous ammonia, ethanolamine, or pyridine solution.

Synthetic polymers such as acetone-formaldehyde condensate, acetone-isobutyraldehyde condensate, methyl ethyl ketone-formaldehyde condensate, poly(allyl alcohol), poly(crotyl alcohol), poly(3-chloroallyl alcohol), ethylene-carbon monoxide copolymers, polyketone from propylene, ethylene and carbon monoxide, poly(methallyl alcohol, poly (methyl vinyl ketone, and poly(vinyl alcohol) have also been cyanoethylated and can also serve as platforms for further modification into metal-binding polymers.

Preferably, the cyanoethylates are derived from sucrose and sorbitol, which are inexpensive and readily available.

The nitrile groups of these cyanoethylates or cyanoalkylates can be reacted with hydroxylamine to form the amidoxime or hydroxamic acid and then further reacted with ammoniacal or ethanolamine solutions of copper to give an amidoxime or hydroxamic acid copper complex that is a deep-blue, water-soluble solution. If hydroxylamine hydrochloride is used instead of hydroxylamine, sodium hydroxide, sodium carbonate or ammonium hydroxide may be used to neutralize the hydrochloric acid. Ammonium hydroxide is preferred.

The reaction can be monitored by IR spectroscopy, where the loss of the nitrile peak at 2250 cm$^{-1}$ and appearance of a new peak at 1660 cm$^{-1}$ is indicative of amidoxime or hydroxamic acid formation. (The IR spectra of an amidoxime and its corresponding hydroxamic acid are not easily distinguished in this region (1600–1700 cm$^{-1}$).)

In the process described herein for preparing wood preservatives, hydroxylamine, hydroxylamine hydrochloride, and hydroxylamine sulfate are suitable sources of hydroxylamine. When hydroxylamine hydrochloride is used as the source of hydroxylamine, a mixture of the amidoxime and hydroxamic acids is generally formed. Since both functional groups form complexes with copper, there is no need to separate the amidoxime and hydroxamic acid compounds before formation of the copper complex.

Preparation of the copper complexes of amidoximes or hydroxamic acids is carried out by adding a solution of Cu(II) salts to an aqueous solution of the amidoxime or hydroxamic acid. Suitable Cu(II) salts include copper sulfate, copper sulfate pentahydrate, cupric chloride, cupric acetate, and basic copper carbonate. The preferred copper salts are copper acetate and copper sulfate.

Figure 1B:
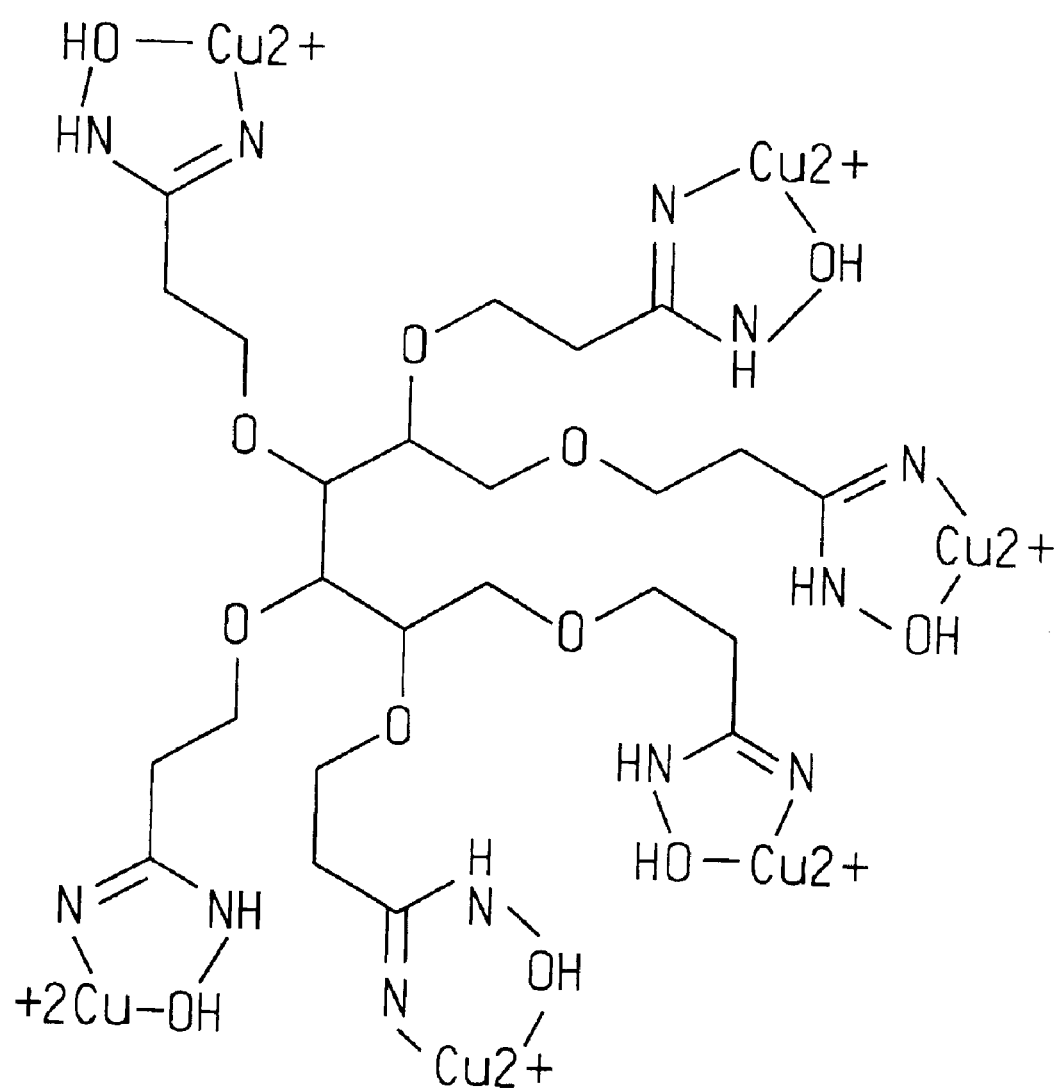
FIG. 1b shows the chemical structure of the copper complex of amidoximes of sorbitol (Cu—Am-Sorb6).

Typical copper complexes produced by the process of this invention, corresponding to the copper complexes of amidoximes of sucrose and sorbitol, are shown in FIG. 1*a* (Cu—Am-Suc7) and FIG. 1*b* (Cu—Am-Sorb6).

Upon addition of a Cu(II) solution to the amidoxime or hydroxamic acid, the solution turns a dark olive-green, and a white precipitate appears on standing. This precipitate can be redissolved by adding ammonium hydroxide, which turns the solution from olive-green to deep blue. To prepare wood imbibement solutions free of insoluble precipitates, an ammoniacal, ethanolamine, or pyridine Cu(II) solution is added directly to the reaction solution containing amidoxime or hydroxamic acid without prior isolation of the amidoxime or hydroxamic acid.

The resulting ammoniacal, ethanolamine, or pyridine solutions are diluted with water to known concentrations of Cu(II). Useful concentrations of copper in these solutions range from 1000 to 9000 ppm copper as determined, for example, by ion-coupled plasma determinations (ICP), and imbibed into wood under the standard pressure treatment process for waterborne preservative systems.

Polymers containing hydroxamic acid groups complex strongly with copper ion and the resulting complexes then bind tenaciously to cellulose. These polymeric compounds are useful for preserving wood.

Cellulosic materials, including newsprint and cardboard samples, treated with copper amidoxime or hydroxamic acid complexes are preserved after being buried in non-sterile soil for 90 days. (Procedure adapted from: Hussey, S. W., More Brownie Girl Scout Try-Its, Girl Scouts of the U.S.A., 81 (1989).) In the same soil, untreated newsprint and cardboard samples were consumed microbially resulting in disintegration of the materials. Given that the composition of mechanically pulped newsprint closely resembles that of coniferous trees (Table 1, U.S. Pat. No. 5,582,682), this method serves as a rapid test for screening for preservatives of wood. The results of the burial test suggest that not only do copper amidoxime or hydroxamic acid complexes preserve cellulose, they also preserve lignin as well and, thus, will preserve wood.

TABLE 1

Compositional Analyses of Cellulosics Expressed in % dry weight.

| Material | Hemicellulose | Cellulose | Lignin |
|---|---|---|---|
| Newsprint | 18 | 55.5 | 25.0 |
| Coniferous Wood | 20–30 | 40–50 | 25–35 |
| Corn Stover | 28.1 | 36.5 | 10.4 |
| Wheat Straw | 50.0 | 30.0 | 15.0 |
| Bagasse | 20.4 | 41.3 | 14.9 |
| Delignified Cellulose Powder | 7.0 | 90–95 | 0.2 |

Similar procedures to those described above can be used to prepare ammoniacal, ethanolamine, or pyridine Cu(II) solutions from compounds that contain at least two functional groups selected from the group of amidoxime, hydroxamic acid, thiohydroxamic acid, N-hydroxyurea, N-hydroxycarbamate, and N-nitroso-alkyl-hydroxylamine functional groups.

GENERAL PROCEDURES

All reactions and manipulations were carried out in a standard laboratory fume hood open to atmosphere. Deionized water was used where water is called for in the subsequent procedures. Sorbitol, acrylonitrile, lithium hydroxide monohydrate, hydroxylamine hydrochloride, copper sulfate pentahydrate, and Chrome Azurol S [1667-99-8] were obtained from Sigma-Aldrich Chemical (Milwaukee, Wis.) and used as received. Concentrated ammonium hydroxide and glacial acetic acid were obtained from EM Science (Gibbstown, N.J.) and used as received. Cyanoethylated sucrose [18307-13-7] and copper acetate monohydrate were obtained from Acros Organics (Geel, Belgium) and used as received. Sucrose was obtained from Pathmark Supermarket (Wilmington, Del.) and used as received. pH was determined with pHydrion paper from Micro Essential Laboratory (Brooklyn, N.Y.). Degree of substitution (DS) of the cyanoethylate is expressed in terms of equivalents of acrylonitrile used in the cyanoethylation step. IR spectra were recorded using a Nicolet Magna 460 spectrometer. LC/MS analyses were performed using a Micromass LCT instrument. NMR spectra were obtained on a Bruker DRX Avance (500 MHz $^1$H, 125 MHz $^{13}$C) using deuterated solvents obtained from Cambridge Isotope Laboratories. ICP measurements were performed using a Perkin Elmer 3300 RL ICP. Elemental analyses were performed by Micro-Analytical Inc, Wilmington, Del. Pressure treatment of southern yellow pine wood was performed in a high-pressure lab using stainless steel pressure vessels following the AWPA standard process (AWPA P5-01).

Abbreviations used herein:

mL = milliliter(s)  
cm = centimeter(s)  
mmol = millimole(s)  
mtorr = millitorr(s)  
min = minute(s)  
AWPA = American Wood Producers Association  
LC/MS = liquid chromatography/mass spectroscopy  
MHz = megahertz  
NMR = nuclear magnetic resonance  
IR = infrared  
ICP = ion coupled plasma  
hr = hour(s)

Cyanoethylation of Sorbitol, DS=1.0 (CE-Sorb1). A one-liter three-necked round-bottomed flask was equipped with a mechanical stirrer, reflux condenser, thermometer, and 100 mL addition funnel under nitrogen. Lithium hydroxide monohydrate (1.0 g, 23.8 mmol, 0.036 eq) dissolved in water (18.5 mL) was added to the flask, followed by the addition of sorbitol (120 g, 659 mmol) in one portion, and then water (100 mL). The solution was warmed to 42° C. in a water bath and treated with acrylonitrile (43.6 mL, 659 mmol, and 1.0 eq) drop-wise via the addition funnel for a period of 2 hr, while maintaining the temperature at 42° C. After the addition was complete, the solution was warmed to 50–55° C. for 4 hr and then allowed to cool to room temperature. The reaction was neutralized by addition of acetic acid (2.5 mL) and allowed to stand overnight at room temperature. The solution was evaporated under reduced pressure to give the product as a clear, viscous oil (155.4 g).

Elemental analysis: Found, 40.95% C; 3.85% N. The IR spectrum showed a nitrile peak at 2255 cm$^{-1}$ indicative of the nitrile group.

Cyanoethylation of Sorbitol, DS=3.0 (CE-Sorb3). A one liter three-neck round-bottomed flask was equipped with a mechanical stirrer, reflux condenser, thermometer, and 100 mL addition funnel under nitrogen. Lithium hydroxide (1.0 g, 23.8 mmol, 0.036 eq) dissolved in water (18.5 mL) was added to the flask, followed by the addition of the first portion of sorbitol (60.0 g, 329 mmol) and then water (50 mL). The solution was warmed to 42° C. in a water bath and treated with acrylonitrile (42 mL, 633 mmol, 0.96 eq) drop-wise via the addition funnel for a period of 1 hr while maintaining the temperature at 42° C. The second portion of sorbitol (60 g, 329 mmol) and water (50 mL) were added to the flask. The second portion of the acrylonitrile (89.1 mL, 1.344 mol, 2.04 eq) was added in a drop-wise fashion over a period of 1 hr. After the addition was complete, the solution was warmed to 50–55° C. for 4 hr and then allowed to cool to room temperature. The reaction was neutralized by addition of acetic acid (2.5 mL) and allowed to stand overnight at room temperature. The solution was evaporated under reduced pressure to give the product as a clear, viscous oil (228.23 g).

Elemental analysis: Found: 49.16% C; 10.76% N. The IR spectrum showed a nitrile peak at 2252 cm$^{-1}$ indicative of the nitrile group.

Cyanoethylatation of Sorbitol, DS=6.0 (CE-Sorb6). A 1000 mL 3-necked round-bottomed flask equipped with an mechanical stirrer, reflux condenser, nitrogen purge, dropping funnel, and thermometer was charged with water (18.5 mL) and lithium hydroxide monohydrate (1.75 g) and the first portion of sorbitol (44.8 g). The solution was heated to 42° C. with a water bath with stirring and the second portion of sorbitol (39.2 g) was added directly to the reaction flask. The first portion of acrylonitrile (100 mL) was then added to the reaction drop-wise via a 500 mL addition funnel over a period of 2 hr. The reaction was slightly exothermic, raising the temperature to 51° C. The final portion of sorbitol (32 g) was added for a total of 0.638 moles followed by a final portion of acrylonitrile (190 mL) over 2.5 hr keeping the reaction temperature below 60° C. (A total of 4.41 moles of acrylonitrile was used.) The reaction solution was then heated to 50–55° C. for 4 hr. The solution was then allowed to cool to room temperature and the reaction was neutralized by addition of acetic acid (2.5 mL). Removal of the solvent under reduced pressure gave the product as a clear, viscous oil (324 g).

The IR spectrum showed a nitrile peak at 2251 cm$^{-1}$, indicative of the nitrile group.

Cyanoethylation of Sucrose, DS=1.0 (CE-Suc1). A 500 mL three-necked round-bottomed flask was equipped with a mechanical stirrer, condenser, and addition funnel under nitrogen. Lithium hydroxide (1.0 g, 23.8 mmol, 0.036 eq) dissolved in water (18.5 mL) was added to the flask, followed by sucrose (120 g, 351 mmol) and water (200 mL). The reaction mixture was heated to 42° C. in a water bath, and acrylonitrile (18.6 g, 351 mmol, 1 eq, 23.2 mL) was added via the addition funnel in a drop-wise fashion over ca. 2 hr, while maintaining the bath temperature at ca. 42° C. After the addition, the reaction mixture was heated at 50–55° C. for 4 hr. The reaction was then allowed to cool to room temperature, neutralized by addition of acetic acid (2.5 mL), and allowed to stand overnight. The solvent was removed under reduced pressure to give the product as a viscous, clear oil (152.7 g).

The IR spectrum showed a nitrile peak at 2255 cm$^{-1}$, indicative of the nitrile group.

Cyanoethylation of Sucrose, DS=4.0 (CE-Suc4). A 500 mL three-necked round-bottomed flask was equipped with a mechanical stirrer, condenser, and addition funnel under nitrogen. Lithium hydroxide (1.0 g, 23.8 mmol, 0.036 eq) dissolved in water (18.5 mL) was added to the flask, followed by sucrose (120 g, 351 mmol) and water (200 mL). The reaction mixture was heated to 42° C. in a water bath, and acrylonitrile (74.4 g, 1.4 mol, 92.8 mL) was added via the addition funnel in a drop-wise fashion over ca. 2 hr, while maintaining the bath temperature at ca. 42° C. After the addition the reaction mixture was heated at 50–55° C. for ca. 4 hr. The reaction mixture was allowed to cool to room temperature, neutralized with acetic acid (2.5 mL), and allowed to stand overnight. The solvent was removed under reduced pressure, maintaining a bath temperature between 50 and 55° C., then pumped at ca. 300 mtorr for ca. 4 hr. The reaction yielded a thick, clear yellow syrup (201.43 g).

The IR spectrum showed a nitrile peak at 2252 cm$^{-1}$, indicative of the nitrile group.

Reaction of CE-Sorb6 with Hydroxylamine Hydrochloride. A 1000 mL three-necked round-bottomed flask was equipped with a mechanical stirrer, condenser, and addition funnel under nitrogen. CE-Sorb6 (14.77 g, 29.5 mmol) and water (200 mL) were added to the flask and stirred. In a separate 500 mL Erlenmeyer flask, hydroxylamine hydrochloride (11.47 g, 165 mmol, 5.6 eq) was dissolved in water (178 mL) and then treated with ammonium hydroxide (22.1 mL of 28% solution, 177 mmol, 6.0 eq) for a total volume of 200 mL. The hydroxylamine solution was then added in one portion directly to the mixture in the round-bottomed flask at room temperature. The stirred mixture was heated at 80° C. for 2 hr, pH=8–9, and then allowed to cool to room temperature.

The IR spectrum indicated loss of most of the nitrile peak at 2250 cm$^{-1}$ and the appearance of a new peak at 1660 cm$^{-1}$, indicative of the amidoxime or hydroxamic acid.

EXAMPLES

Example 1

Preparation of Copper Complex of the Amidoxime of Sorbitol

A solution of copper sulfate pentahydrate (14.77 g, 165 mmol, 5.6 eq) in water (200 mL) was added rapidly via addition funnel to the ammonia-containing solution of the product of the reaction of CE-Sorb6 with hydroxylamine hydrochloride (as described above). Initially, the solution turned a dark green and contained some solids. A blue color appeared upon further addition of the copper solution, and quickly dissipated on stirring. Additional ammonium hydroxide (19.7 g, 152 mmol) was added via pipette during the course of the addition of the copper solution. The resulting dark blue solution was stirred overnight, pH 8–9, and then diluted with water to a total volume of 2100 mL (theor.=5000 ppm Cu).

ICP Analysis of 100:1 solution: 45.1 ppm Cu.

Example 2

Preparation of Copper Complexes of Polyhydroxamic Acid

The preparation of polymeric hydroxamic acid compounds is essentially that as described in U.S. Pat. No. 3,488,329. That process was modified by using hydroxylamine water solution, instead of by neutralizing aqueous hydroxylamine by addition of base to hydroxylamine hydrochloride.

Poly(methyl vinyl ether)-maleic anhydride copolymer (5 g) was suspended in 20 g of water and to this was added 2.2 g of triethylamine or 1.8 g of pyridine. To this suspension was added 1.5 g of hydroxylamine as a 50 wt % solution in water. The solution became warm and was allowed to stir overnight at room temperature. Aqueous solutions of 3 g copper chloride, 5.2 g copper nitrate, or 4.5 g of copper acetate were prepared in 10 mL of water and then added to the polymer solution followed by 8.2 g of concentrated ammonium hydroxide.

The resulting blue solutions could be imbibed into wood.

Example 3

Procedure for Laboratory Imbibement of SYP Wood

Using standard laboratory glassware and a vacuum pump, a wood impregnation system as described in AWPA Standard E10-01 was used to imbibe small pre-weighed Southern Yellow Pine (SYP) wood blocks (¾"×¾"×¾"). The imbibement vessel was evacuated for 15 min and then the vacuum was broken by introduction of the imbibement solution. The imbibement solution was prepared by diluting the preparations given in Example 1 with water to a copper concentration of 5000 ppm. The blocks were imbibed under atmospheric pressure for 15 minutes. The blocks were allowed to drip dry and were then weighed wet to ensure that the wood was penetrated with the imbibement solution. The blocks were then dried overnight in a convection oven at 55° C. Weights of the dried blocks were then recorded.

Example 4

Procedure for High Pressure Imbibement of SYP Wood

Two pre-weighed SYP wooden stakes (¾"×¾"×12" or ¾"×1½"×12") were loaded into a hastaloy pressure vessel and covered with imbibement solution at room temperature. The imbibement solution was prepared by diluting the preparations given in Example 1 with water to a copper concentration of 5000 ppm. The vessel was evacuated for 5 min and then pressured with nitrogen for 1 h at 155 psi at which time the pressure was removed. The stakes were then removed from the vessel and allowed to drip dry. Weights were then recorded to insure that the wood was penetrated with the imbibement solution. The stakes were then dried overnight in a convection oven at 55° C. Weights of the dried stakes were then recorded.

These treated stakes along with control (untreated) stakes were labeled and buried in a flower pot with about ¾ of the wood below the surface of non-sterile soil. The flower pots were kept moist in a greenhouse at 78° C. After 5 months, the stakes were visually examined. The untreated control stakes showed a covering of white, hairy fungus on the wood that was below the surface of the soil, whereas the treated stakes showed no such covering.

Example 5

Ground Burial Exposure

The imbibement solution was prepared by diluting the preparations given in Example 1 with water to a copper concentration of 5000 ppm. Samples of newsprint were soaked in solutions of the copper complexes for 5 min. The paper was removed from the imbibing solution, blotted nearly dry, air-dried overnight, and then placed in sacks made from nylon stockings. The sacks were labeled and closed with nylon twist-ties. Control samples of untreated newsprint were placed in similar nylon sacks. The sacks of treated and untreated newsprint were buried in clay pots containing moist, non-sterile garden soil for 90 days and maintained at approximately 18 to 24° C. After 90 days the sacks were unburied, opened, and the contents examined for decomposition.

Untreated newsprint was essentially completely decomposed. Treated newsprint was still intact and the printing was still legible.

What is claimed is:

1. A wood preservative composition comprising an aqueous solution of:
   a. a copper complex of a chelating compound comprising at least two functional groups selected from the group consisting of amidoxime, hydroxamic acid, thiohydroxamic acid, N-hydroxyurea, N-hydroxycarbamate, and N-nitroso-alkyl-hydroxylamine; and
   b. ammonia, ethanolamine, or pyridine in an amount sufficient to solubilize the copper complex.

2. The wood preservative composition of claim 1, wherein the at least two functional groups are amidoxime or hydroxamic acid derived from a cyanoethylated compound.

3. The wood preservative composition of claim 2, wherein the cyanoethylated compound is derived from the cyanoethylation of:
   a. a primary amine, a secondary amine, blood albumin, casein, gelatin, gluten, soybean protein, wool, or corn zein; or
   b. materials derived from blood albumin, casein, gelatin, gluten, soybean protein, wool, or corn zein.

4. The wood preservative composition of claim 2, wherein the cyanoethylated compound is derived from the cyanoethylation of synthetic polymers selected from the group consisting of acetone-formaldehyde condensate; acetone-isobutyraldehyde condensate; methyl ethyl ketone-formaldehyde condensate; poly(allyl alcohol); poly(crotyl alcohol); poly(3-chloroallyl alcohol); ethylene-carbon monoxide copolymers; polyketone from propylene, ethylene and carbon monoxide; poly(methallyl alcohol); poly(methyl vinyl ketone); and poly(vinyl alcohol).

5. The wood preservative composition of claim 2, wherein the cyanoethylated compound is obtained from the cyanoethylation of materials selected from the group consisting of:
   a. alcohols, carbohydrates, dextran, dextrin, gums, starches, modified natural polymers; and
   b. compounds derived from natural polymers.

6. The wood preservative composition of claim 2, wherein the cyanoethylated compound is obtained from the cyanoethylation of sucrose or sorbitol.

7. The wood preservative composition of claim 5, wherein the gums are selected from the group consisting of guar, locust bean, honey locust, flame tree, tara, arabic, tragacanth, and karaya gums.

8. The wood preservative composition of claim 5, wherein the starches are selected from the group consisting of starches derived from corn, potato, tapioca, or wheat.

9. The wood preservative composition of claim 5, wherein the modified natural polymers are selected from the group consisting of regenerated cellulose, cellulose xanthate, dimethylthiourethane of cellulose, ethyl cellulose, ethylthiourethane of cellulose, hydroxyethylcellulose, methylcellulose, and phenylthiourethane of cellulose.

10. The wood preservative composition of claim 5, wherein the natural polymer is selected from the group consisting of flax, jute, sisal, and manila.

11. The wood preservative composition of claim 1, wherein the chelating compound comprises at least two amidoxime or hydroxamic acid groups, and the chelating compound is derived from polyacrylonitrile, or from a copolymer of acrylonitrile and vinyl monomers.

12. The wood preservative composition of claim 1, wherein the chelating compound comprises at least two hydroxamic groups and the chelating compound is derived from styrene-maleic anhydride or poly(vinylmethylether/maleic anhydride) copolymers.

13. A process for preparing a copper complex, comprising:
   a. forming an aqueous mixture of a cyanoethylation catalyst and an alcohol or amine;
   b. adding an unsaturated nitrile to the aqueous mixture of (a) and allowing the unsaturated nitrile to react with the alcohol or amine to form a first aqueous solution;
   c. adding i) a source of hydroxylamine, and ii) ammonium hydroxide, ethanolamine, or pyridine to the first aqueous solution of step (b) to form a second aqueous solution; and
   d. adding a source of Cu(II) to the second aqueous solution of step (c) to form a copper complex.

14. The process of claim 13, wherein the alcohol is sucrose or sorbitol.

15. The process of claim 13, wherein the amine is a primary or secondary amine having 1 to 30 carbon atoms, or is polyethyleneamine.

16. The process of claim 13, wherein the source of hydroxylamine is hydroxylamine, hydroxylamine hydrochloride, or hydroxylamine sulfate.

17. The process of claim 13, wherein the cyanoethylation catalyst is a catalytically effective amount of lithium hydroxide, sodium hydroxide, or potassium hydroxide.

18. The process of claim 13, wherein the unsaturated nitrile is acrylonitrile.

19. The process of claim 13, wherein the source of Cu(II) is selected from the group consisting of copper sulfate, copper sulfate pentahydrate, cupric chloride, cupric acetate, and basic copper carbonate.

20. A process for preparing a wood preservative composition, comprising contacting an aqueous solution comprising a copper salt, at least one chelating compound comprising at least two functional groups selected from the group consisting of amidoxime, hydroxamic acid, thiohydroxamic acid, N-hydroxyurea, N-hydroxycarbamate, and N-nitroso-alkyl-hydroxylamine, with ammonia, ethanolamine, or pyridine.

21. A process for preserving an article, comprising contacting an article selected from the group consisting of wood, lumber, plywood, oriented strand board, cellulose, hemicellulose, lignin, cotton, and paper with the wood preservative composition of claim 1.

22. The process of claim 21, wherein contacting comprises dipping, brushing, spraying, draw-coating, rolling, or pressure-treating.

23. The process of claim 21, wherein the article is wood or lumber.

24. The process of claim 21, further comprising subjecting the wood or lumber to vacuum both before and after contacting the wood or lumber with the wood preservative composition of claim 1.

25. An article treated with the wood preservative composition of claim 1.

26. The article of claim 25, wherein the article is selected from the group consisting of wood, paper, cellulose, cotton, lignin, and hemicellulose.

27. An article the comprising:
   a) wood, lumber, plywood, oriented strandboard, paper, cellulose, cotton, lignin or hemicellulose;
   b) copper; and
   c) at least one chelating compound, wherein the chelating compound comprises at least two functional groups selected from the group consisting of amidoxime, hydroxamic acid, thiohydroxamic acid, N-hydroxyurea, N-hydroxycarbamate, and N-nitroso-alkyl-hydroxylamine.

* * * * *

UNITED STATES PATENT AND TRADEMARK OFFICE
CERTIFICATE OF CORRECTION

PATENT NO.   : 6,978,724 B2  
DATED        : December 27, 2005  
INVENTOR(S)  : Anderson, Albert Gordon, Feaster, John E. and Scialdone, Mark A.

Page 1 of 1

It is certified that error appears in the above-identified patent and that said Letters Patent is hereby corrected as shown below:

<u>Title page,</u>
Item [75], Inventors, add -- John E. Feaster (Chesapeake City, MD) --.

Signed and Sealed this

Eleventh Day of April, 2006

JON W. DUDAS
*Director of the United States Patent and Trademark Office*